(12) United States Patent
King et al.

(10) Patent No.: US 11,891,729 B2
(45) Date of Patent: Feb. 6, 2024

(54) MACHINE-KNITTABLE CONDUCTIVE HYBRID YARNS

(71) Applicant: Propel, LLC, Pawtucket, RI (US)

(72) Inventors: Clare King, Providence, RI (US); Anjali Khemani, Providence, RI (US); Birgit Leitner, Providence, RI (US)

(73) Assignee: Propel, LLC, Pawtucket, RI (US)

( * ) Notice: Subject to any disclaimer, the term of this patent is extended or adjusted under 35 U.S.C. 154(b) by 102 days.

(21) Appl. No.: 16/845,796

(22) Filed: Apr. 10, 2020

(65) Prior Publication Data

US 2021/0277544 A1 Sep. 9, 2021

Related U.S. Application Data

(60) Provisional application No. 62/832,098, filed on Apr. 10, 2019, provisional application No. 62/832,104,
(Continued)

(51) Int. Cl.
*D02G 3/36* (2006.01)
*D02G 3/44* (2006.01)
(Continued)

(52) U.S. Cl.
CPC .............. *D02G 3/36* (2013.01); *D02G 3/045* (2013.01); *D02G 3/047* (2013.01); *D02G 3/12* (2013.01);
(Continued)

(58) Field of Classification Search
CPC .......... D02G 3/045; D02G 3/047; D02G 3/12; D02G 3/36; D02G 3/441; D02G 3/443; D10B 2501/00; D10B 2401/16
See application file for complete search history.

(56) References Cited

U.S. PATENT DOCUMENTS 3,472,289 A * 10/1969 Riordan ................. D02G 3/441
139/425 R
4,262,480 A * 4/1981 Wasserman ............ D02G 3/343
428/377
(Continued)

FOREIGN PATENT DOCUMENTS

CN 105209673 A 12/2015
EP 0458343 A1 11/1991
(Continued)

OTHER PUBLICATIONS

Https://www.dupont.com/content/dam/dupont/amer/us/en/safety/public/documents/en/Kevlar_Technical_Guide_0319.pdf, retrieved Jul. 6, 2022.*
(Continued)

*Primary Examiner* — Shaun R Hurley
(74) *Attorney, Agent, or Firm* — Nutter McClennen & Fish LLP

(57) ABSTRACT

A machine knittable hybrid yarn for providing conductive traces through a textile is disclosed. The hybrid yarn includes conductive wires coated with an insulating material and twisted together with a nonconductive yarn. The nonconductive yarn is from a strong, inelastic, and nonconductive fiber, such as a meta-aramid or para-aramid that protects the integrity of the conductive wire during knitting. The conductive wire can be copper-clad stainless steel or copper wire is coated with polyurethane, and the nonconductive yarn can have no-drip and no-drip properties to allow ablation of the hybrid yarn to remove the conductive yarn and insulating coating on the wire such that the ablated region becomes externally conductive and suitable for making an electrical contact. The hybrid yarn can be bonded with nylon or similar polymer after twisting.

107 Claims, 11 Drawing Sheets

Related U.S. Application Data filed on Apr. 10, 2019, provisional application No. 62/832,101, filed on Apr. 10, 2019.

(51) Int. Cl.
*D02G 3/04* (2006.01)
*D02G 3/12* (2006.01)
*A61B 5/00* (2006.01)
*D04B 1/12* (2006.01)
*D03D 1/00* (2006.01)
*H05K 1/03* (2006.01)
*A61B 5/25* (2021.01)
*A61B 5/27* (2021.01)

(52) U.S. Cl.
CPC ............. *D02G 3/441* (2013.01); *D02G 3/443* (2013.01); *A61B 5/25* (2021.01); *A61B 5/27* (2021.01); *A61B 5/6804* (2013.01); *A61B 2562/14* (2013.01); *D03D 1/0088* (2013.01); *D04B 1/12* (2013.01); *D04B 1/126* (2013.01); *D10B 2211/02* (2013.01); *D10B 2401/16* (2013.01); *D10B 2403/02431* (2013.01); *D10B 2501/00* (2013.01); *H05K 1/038* (2013.01); *H05K 2201/0281* (2013.01)

(56) References Cited

U.S. PATENT DOCUMENTS

| | | |
|---|---|---|
| 4,640,689 A | 2/1987 | Sibalis |
| 4,868,580 A * | 9/1989 | Wade .................. D02G 3/12 343/912 |
| 4,926,910 A * | 5/1990 | Wade .................. D02G 3/12 139/425 R |
| 5,193,607 A | 3/1993 | Demukai et al. |
| 5,288,289 A | 2/1994 | Haak et al. |
| 5,927,060 A * | 7/1999 | Watson .................. D02G 3/38 57/210 |
| 6,941,775 B2 | 9/2005 | Sharma |
| 7,133,227 B2 | 11/2006 | Chiang et al. |
| 7,308,294 B2 | 12/2007 | Hassonjee et al. |
| 7,319,895 B2 | 1/2008 | Klefstad-Sillonville et al. |
| 7,592,276 B2 | 9/2009 | Hill et al. |
| 7,779,656 B2 | 8/2010 | Dias et al. |
| 8,060,175 B2 | 11/2011 | Rowlandson et al. |
| 8,214,008 B2 | 7/2012 | Hassonjee et al. |
| 8,283,563 B2 | 10/2012 | Harris et al. |
| 8,505,474 B2 | 8/2013 | Kang et al. |
| 8,934,957 B2 | 1/2015 | Dias et al. |
| 9,186,092 B2 | 11/2015 | Mestrovic et al. |
| 9,388,514 B2 | 7/2016 | Roh |
| 9,801,583 B2 | 10/2017 | Derchak et al. |
| 10,011,925 B2 | 7/2018 | Kurahashi et al. |
| 10,070,815 B2 | 9/2018 | Shoshani et al. |
| 10,144,193 B2 | 12/2018 | Haraikawa et al. |
| 10,155,274 B2 | 12/2018 | Robinson et al. |
| 10,299,520 B1 | 5/2019 | Shaffer et al. |
| 10,301,751 B2 | 5/2019 | Dias et al. |
| 10,448,680 B2 | 10/2019 | Howland |
| 10,462,898 B2 | 10/2019 | Longinotti-Buitoni et al. |
| 10,480,104 B2 | 11/2019 | Fu et al. |
| 10,480,106 B2 | 11/2019 | Krajewski et al. |
| 10,485,103 B1 | 11/2019 | Sunshine et al. |
| 10,492,302 B2 | 11/2019 | Karagozler et al. |
| 10,503,339 B2 | 12/2019 | Karagozler |
| 10,519,575 B2 | 12/2019 | Thompson et al. |
| 10,754,486 B2 * | 8/2020 | Cobanoglu .......... G06F 3/0448 |
| 2004/0057176 A1 * | 3/2004 | Dhawan .................. D02G 3/38 361/62 |
| 2005/0034485 A1 * | 2/2005 | Klefstad-Sillonville .................... A61B 5/4818 66/171 |
| 2005/0231207 A1 * | 10/2005 | Goldwater ............. D07B 1/145 324/522 |
| 2006/0218778 A1 | 10/2006 | Jawahar et al. |
| 2007/0083096 A1 | 4/2007 | Paradiso |
| 2007/0281155 A1 * | 12/2007 | Tao .................. A47H 21/00 428/365 |
| 2008/0044652 A1 * | 2/2008 | Krans ................... D02G 3/441 428/364 |
| 2008/0282665 A1 * | 11/2008 | Speleers .................. D02G 3/12 57/212 |
| 2009/0018428 A1 | 1/2009 | Dias et al. |
| 2010/0084179 A1 | 4/2010 | Harris et al. |
| 2010/0199901 A1 * | 8/2010 | Kang ...................... D02G 3/12 112/439 |
| 2012/0100386 A1 * | 4/2012 | Honma .................. D02G 3/441 428/592 |
| 2012/0225275 A1 * | 9/2012 | Honma .................. D02G 3/12 428/222 |
| 2013/0302605 A1 | 11/2013 | Yang et al. |
| 2014/0223650 A1 | 8/2014 | Hines et al. |
| 2014/0262478 A1 * | 9/2014 | Harris .................... H05K 9/009 174/393 |
| 2014/0363656 A1 * | 12/2014 | Kunisada ............... D02G 3/441 428/221 |
| 2015/0087925 A1 | 3/2015 | Pedley et al. |
| 2015/0297135 A1 | 10/2015 | Shoshani et al. |
| 2016/0018274 A1 | 1/2016 | Seitz |
| 2016/0145776 A1 * | 5/2016 | Roh ....................... D02G 3/441 57/211 |
| 2016/0284436 A1 | 9/2016 | Fukuhara et al. |
| 2017/0073172 A1 | 3/2017 | Kuijpers et al. |
| 2017/0079348 A1 | 3/2017 | Chahine et al. |
| 2017/0107647 A1 * | 4/2017 | Riethmuller ............. D04B 1/14 |
| 2017/0275789 A1 * | 9/2017 | Dias ..................... D02G 3/22 |
| 2018/0042551 A1 | 2/2018 | Gouthez et al. |
| 2018/0073172 A1 | 3/2018 | Kurahashi et al. |
| 2018/0085060 A1 | 3/2018 | Shoshani et al. |
| 2018/0087191 A1 | 3/2018 | Threlkeld |
| 2018/0151795 A1 * | 5/2018 | Cobanoglu .......... H01L 41/193 |
| 2018/0195210 A1 * | 7/2018 | Sunshine ............... D02G 3/441 |
| 2018/0195218 A1 | 7/2018 | Hamada et al. |
| 2018/0195985 A1 * | 7/2018 | Nebuya ..................... G01N 27/06 |
| 2018/0249767 A1 | 9/2018 | Begriche et al. |
| 2018/0258562 A1 * | 9/2018 | Fukuhara ............ D03D 1/0088 |
| 2018/0279930 A1 | 10/2018 | Coppede et al. |
| 2019/0003083 A1 * | 1/2019 | Carlsson ................. D02G 3/12 |
| 2019/0055678 A1 * | 2/2019 | Hightower, III ......... D02G 3/36 |
| 2019/0156972 A1 | 5/2019 | Kondo et al. |
| 2019/0354242 A1 * | 11/2019 | Cobanoglu .......... D03D 1/0088 |
| 2020/0123689 A1 * | 4/2020 | Zhang .................. D03D 25/005 |
| 2020/0199790 A1 * | 6/2020 | Hayashi ................. D02G 3/36 |
| 2020/0270775 A1 * | 8/2020 | Oppenheim ............. H01B 7/17 |
| 2020/0323491 A1 | 10/2020 | King et al. |
| 2020/0325603 A1 | 10/2020 | King et al. |
| 2020/0345083 A1 * | 11/2020 | Threlkeld ................. D02G 3/12 |
| 2020/0347527 A1 * | 11/2020 | Konukoglu .............. D02G 3/32 |
| 2021/0207294 A1 * | 7/2021 | Threlkeld ................ D02G 3/36 |

FOREIGN PATENT DOCUMENTS

| | | |
|---|---|---|
| EP | 1482079 B1 | 7/2007 |
| EP | 3090082 B1 | 11/2017 |
| FR | 3061851 A1 | 7/2018 |
| NO | 2019/143694 A1 | 7/2019 |
| SK | 2082017 U1 | 4/2018 |
| WO | 2001/002052 A2 | 1/2001 |
| WO | 2014/138204 A1 | 9/2014 |
| WO | 2014/165997 A1 | 10/2014 |
| WO | 2015/022671 A1 | 2/2015 |
| WO | 2017/095861 A1 | 6/2017 |
| WO | 2017/111687 A1 | 6/2017 |
| WO | 2018/020169 A1 | 2/2018 |
| WO | 2018/128584 A1 | 7/2018 |

(56) References Cited

FOREIGN PATENT DOCUMENTS

| WO | 2019/134031 A2 | 7/2019 |
|---|---|---|
| WO | 2019/145891 A1 | 8/2019 |

OTHER PUBLICATIONS

Https://www.teijinaramid.com/wp-content/uploads/2016/07/Product-Brochure-Twaron.pdf, retrieved Jul. 6, 2022.*
International Search Report and Written Opinion for International Application No. PCT/US2020/027697, dated Jul. 9, 2020 (14 pages).
International Search Report and Written Opinion for International Application No. PCT/US2020/027699, dated Jul. 9, 2020 (13 pages).
International Search Report and Written Opinion for International Application No. PCT/US2020/027695, dated Jul. 23, 2020 (13 pages).
Weder, et al. Embroidered Electrode with Silver/Titanium Coating for Long-Term ECG Monitoring. Sensors 15, pp. 1750-1759, 2015. Retrieved from the Internet under https://www.mdpl.com/1424-8220/15/1/1750 on Mar. 23, 2020.
U.S. Appl. No. 16/845,772, filed Apr. 10, 2020, Knitted Textiles With Conductive Traces of a Hybrid Yarn and Methods of Knitting the Same.
U.S. Appl. No. 16/845,781, filed Apr. 10, 2020, Systems for Maintaining Moisture in a Textile Electrode.
International Preliminary Report on Patentability for International Application No. PCT/US2020/027695, dated Sep. 28, 2021 (11 pages).
International Preliminary Report on Patentability for International Application No. PCT/US2020/027697, dated Sep. 28, 2021 (8 pages).
International Preliminary Report on Patentability for International Application No. PCT/US2020/027699, dated Sep. 28, 2021 (11 pages).
Northolt, M. (1989). The Structure and Properties of Aramid Fibres. In: Bunsell, A.R., Lamicq, P., Massiah, A. (eds) Developments in the Science and Technology of Composite Materials, Springer, Dordrecht, Chapter 44, 2 pages (Abstract).
Supplementary European Search Report for EP Application No. 20786809.2, PCT/US2020/027699 dated Nov. 21, 2022 (8 pages).

* cited by examiner

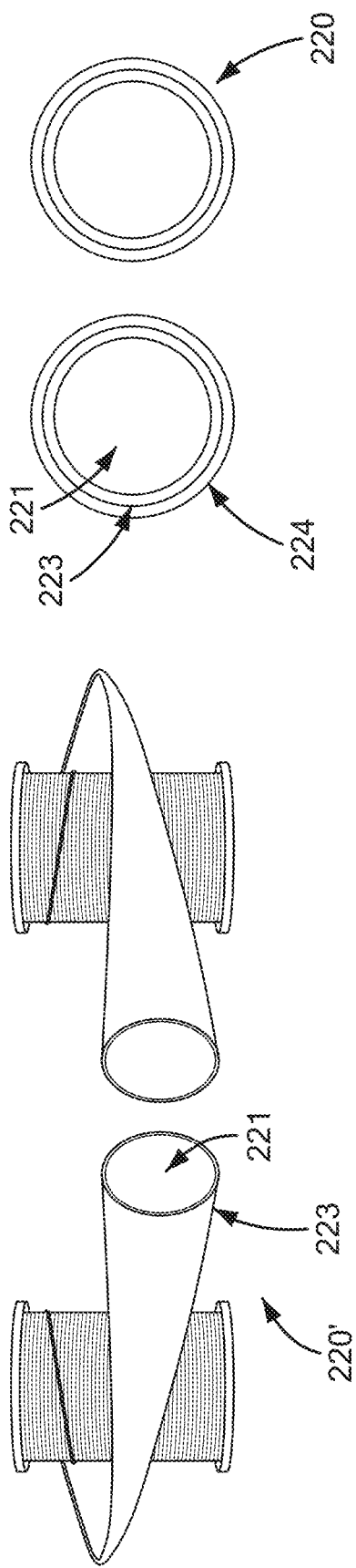
FIG. 4A
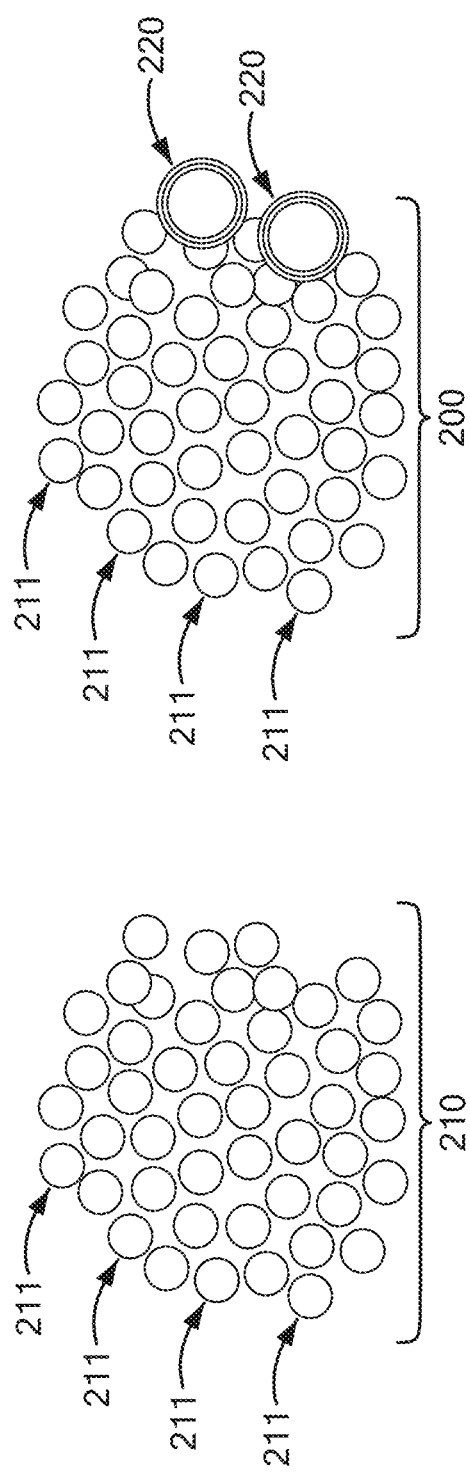
FIG. 4B
FIG. 4D
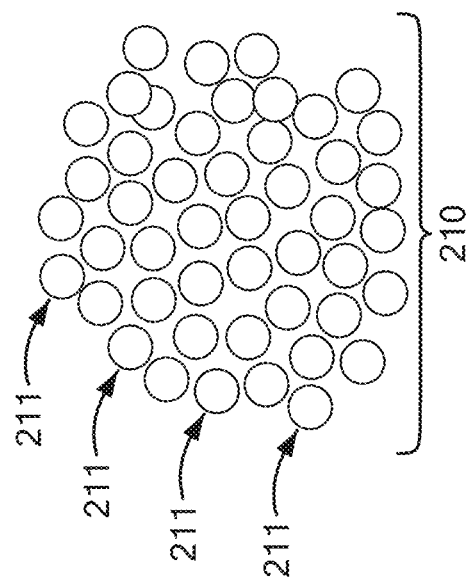
FIG. 4C

MACHINE-KNITTABLE CONDUCTIVE HYBRID YARNS

CROSS-REFERENCE TO RELATED APPLICATIONS

This application claims priority from U.S. Provisional Application Ser. No. 62/832,098 filed Apr. 10, 2019 and entitled GARMENTS WITH INTEGRATED ELECTRODES AND CONDUCTIVE TRACES; from U.S. Provisional Application Ser. No. 62/832,101 filed Apr. 10, 2019 and entitled SYSTEMS AND METHODS FOR MAINTAINING MOISTURE IN A TEXTILE ELECTRODE; and from U.S. Provisional Application Ser. No. 62/832,104 filed Apr. 10, 2019 and entitled HYBRID YARN FOR WEAVING CONDUCTIVE WIRES INTO FABRIC. The contents of U.S. Provisional Application Ser. No. 62/832,098, U.S. Provisional Application Ser. No. 62/832,104, and U.S. Provisional Application Ser. No. 62/832,101 are hereby incorporated in their entireties by reference.

The subject matter of this patent application may be related to the subject matter of U.S. patent application Ser. No. 16/845,772 entitled KNITTED TEXTILES WITH CONDUCTIVE TRACES OF A HYBRID YARN AND METHODS OF KNITTING THE SAME filed on even date herewith and U.S. patent application Ser. No. 16/845,781 entitled SYSTEMS FOR MAINTAINING MOISTURE IN A TEXTILE ELECTRODE filed on even date herewith. Each of these patent applications is hereby incorporated herein by reference in its entirety.

GOVERNMENT RIGHTS

This invention was made with Government support under Grant No. N00189-17-C-Z023 awarded by the U.S. Navy. The Government has certain rights in the invention.

FIELD

This disclosure relates to a multi-element yarn constructed from an inelastic yarn and a coated conductive wire for use in transmitting electrical signals in textiles.

BACKGROUND

Existing efforts to provide a fabric with electrically conductive properties have involved providing a hybrid yarn in which conductive metal components, typically fine wires, are covered or wrapped with non-conductive fibers. While the resulting hybrid yarns have electrical properties, these hybrid yarns are best suited for using with sewing or embroidery techniques in order to impart electrical properties to a textile. It may also be feasible to weave a fabric with such hybrid yarns. However, it is typically not possible to knit textiles, and, in particular, textiles suitable for garments such as next-to-skin garments, with these hybrid covered yarns as the yarns are typically too large for knitting fine gauge textiles (e.g., 12-40 gauge), or too stiff and inelastic to accommodate to the knitting process. The stiffness and inelasticity results in existing hybrid yarns forming kinks in the knit structures that limit their use as garment textiles, or the hybrid yarns causing the knitting needles in the knitting machine to break frequently making knitting operations unachievable.

Another approach was the development of a hybrid yarn in which an elastic nonconductive core is wrapped with the inelastic metal wire. These solutions typically attempt to mitigate the similarly inherent inelastic nature of the metals incorporated with the hybrid yarn to give it conductive properties by altering the construction of the hybrid yarn such that elastic lengthening of the nonconductive yarn does not break the contained conductive wires. However, these hybrid elastic yarns are typically too large for knitting and the same knitting needle breaking issues are also an issue. The above deficiencies are addressed by the present disclosure by developing a hybrid yarn that is suitable for knitting operations in the 7 to 40 gauge range.

SUMMARY

Certain embodiments of the present disclosure provide a hybrid yarn constructed from one or more conductive wires coated with an insulating material and twisted together with a nonconductive yarn. This hybrid yarn can be composed of at least one fine conductive wire that is twisted using traditional yarn twisting equipment with a yarn of strong, inelastic, and nonconductive fiber, such as a meta-aramid or para-aramid. The meta-aramid or para-aramid yarn may be a filament yarn, but is more typically a staple yarn. The meta or para-aramid content can be 100% but blends in the range of 70% meta-aramid or para-aramid and 30% other yarns are also acceptable, where the other yarns can be selected from fibers typically used in yarns suitable for clothing, such as wool, nylon, polyester, acrylic, aramid, modacrylic or other similar fibers. In some instances, the nonconductive yarn is a para-aramid such as Kevlar, or a similarly high strength and low elasticity material. In some instances, the conductive wire is coated with polyurethane or a similar material. In some instances, the conductive wire is copper-clad stainless steel or copper wire. In some instances, the conductive wire is twisted with the nonconductive yarn at between 5 and 12 twists per inch. In some instances, the nonconductive yarn is approximately suitable for a 15 gauge knitting machine. In some instances, the conductive wire is approximately 50 microns with a 3-4 micron coating. In some instances, one or more individual strands of coated conductive wire are twisted with a single strand of nonconductive yarn.

Certain embodiments of the present disclosure include a machine-knittable hybrid yarn, having a non-conductive yarn and a conductive wire twisted with the nonconductive yarn, with the conductive wire having an exterior layer of an insulating material. In some embodiment, non-conductive yarns are twisted together with the conductive wire. The non-conductive yarn and the conductive wire can be twisted together, for example, with Z twist or an S twist from a single twisting process. such that, for example, the fibers of the non-conductive yarn are twisted together before being twisted with the conductive wire to form the hybrid yarn. In some embodiments, the conductive wire is twisted with the conductive yarn at between 1 and 15 twists per inch. In some embodiments, the conductive wire is twisted with the conductive yarn at between 5 and 12 twists per inch. The conductive wire can be defined as a continuous strand of metal along the hybrid yarn. The hybrid yarn can be bonded with a polymer coating, which can be Nylon. The insulating layer can include a polymer coating, such as polyurethane.

In some embodiments, the nonconductive yarn is 1500 denier or finer. The conductive wire can be approximately 10 to 100 microns thick. In some embodiments, non-conductive yarn has an elasticity less than that of the twisted conductive wire such that the conductive wire does not break before the non-conductive yarn under tensile loading of the hybrid yarn during a machine knitting process. In some embodiments, the non-conductive yarn has a tensile strength higher than the conductive wire, and, in some embodiments, the non-conductive yarn has a Young's modulus of at least 60 GPa. In some embodiments, the nonconductive yarn has a break elongation percentage of 4.2 or less In some embodiments, the non-conductive yarn is fire retardant and self-extinguishing. For example, in some embodiments, the non-conductive yarn is no-melt and no-drip according to the ASTM D6413/D6413M Standard Vertical Test Method for Flame Resistance of Textiles.

The non-conductive yarn can be made from at least one of an aramid, meta-aramid, or para-aramid polyamide fibers, which can include staple fibers. The conductive wire can be a copper-clad stainless steel wire or a solid copper wire. In some embodiments, the non-conductive yarn and the insulating material have a decomposition temperature less than a melting point of the conductive wire.

The conductive wire can be a first conductive wire and the hybrid yarn further include a one or more additional conductive wires twisted with the nonconductive yarn.

Another embodiment of the present disclosure is a machine-knittable hybrid yarn, having a non-conductive yarn, which can itself be twisted or untwisted and a conductive wire twisted together with the nonconductive yarn, the conductive wire having an exterior coated with an insulating material, with wherein the non-conductive yarn having a tensile strength higher than the conductive wire, and the non-conductive yarn being fire retardant and self-extinguishing.

Yet another embodiment is a method of making a machine-knittable hybrid yarn, the method including twisting, in a single process, twisting a non-conductive yarn of a non-conductive yarn with a conductive wire, the conductive wire having an exterior layer of an insulating material. The method can include the conductive wire being twisted together with the non-conductive yarn at between 1 and 15 twists per inch. In some embodiments, the non-conductive yarn has an elasticity less an effective elasticity of the twisted conductive wire such that the conductive wire does not break before the non-conductive yarn under tensile loading of the hybrid yarn. In some embodiments, the non-conductive yarn is fire retardant and self-extinguishing.

In some embodiments, the non-conductive yarn has a tensile strength higher than the conductive wire. The non-conductive yarn can have a Young's modulus of at least 60 GPa and up to, in some embodiments, 179 GPa. The nonconductive yarn can have a break elongation percentage of 4.2 or less. In some embodiments, the non-conductive yarn comprises at least one of an aramid, meta-aramid, or para-aramid polyamide fiber. In some embodiments, the conductive wire comprises a copper-clad stainless steel wire or a solid copper wire. In some embodiments, the non-conductive yarn comprises staple fibers Other embodiments, features, and advantages of the subject matter included herein will be apparent from the description and drawings, and from the claims.

BRIEF DESCRIPTION OF THE DRAWINGS

This disclosure will be more fully understood from the following detailed description taken in conjunction with the accompanying drawings, in which:

FIGS. 4A-4F are schematic illustration of an example construction steps for making an example hybrid yarn;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Example Textiles with Integrated Conductive Traces

Figure 1A:
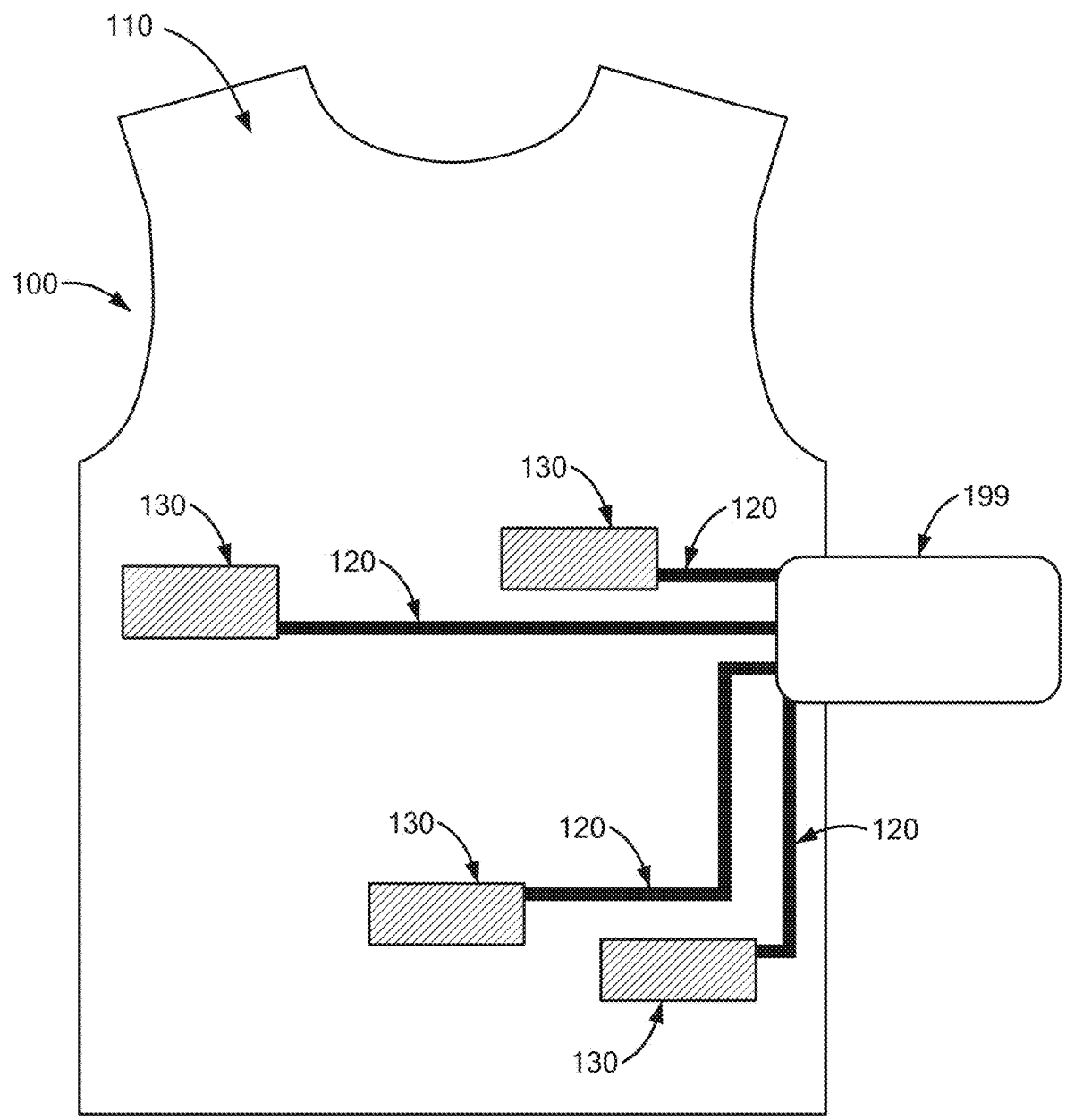
FIG. 1A is a schematic illustration of a single-layer textile formed as a wearable garment with integrated textile electrodes and conductive traces connecting the electrodes to a controller unit configured in accordance with illustrative embodiments.

FIG. 1A is a schematic illustration of a textile formed as a wearable garment with integrated electrodes and conductive traces connecting the electrodes to a controller unit configured in accordance with illustrative embodiments. Specifically, FIG. 1A schematically shows a textile garment 100 with integrated textile electrodes 130, and conductive traces 120 connecting the textile electrodes 130 to an electrical device 199. The garment 100 is constructed as a single textile layer to be worn directly against the skin. The garment 100 is knitted from a regular electrically inert material 110 (e.g., an insulator material, such as cotton, wool, or polyester) with the textile electrodes 130 knitted directly into the garment 100, without adding additional textile layers at the location of the textile electrodes 130. The conductive traces 120 are knitted with a hybrid yarn, discussed in more detail below, that is constructed from a strong and inelastic nonconductive yarn twisted with one or more conductive wires, with the conductive wires being coated with an insulating material. The hybrid yarn enables the conductive traces 120 to transmit power or electrical signals through the conductive wires without interference due to the insulating coating on the conductive wires. The textile electrodes 130 have an inner surface that is therefore positioned against the user's skin when the garment 100 is worn. The textile electrodes 130 are knitted from a conductive yarn, such as a silver coated polyester, that enables the textile electrodes 130 to conduct electrical signals across the textile electrode 130. The textile electrodes 130 are connected to the electrical device 199 via conductive traces 120 that are also knitted directly into the garment 100 without adding additional layers to the garment. In some embodiments, the garment 100 defines a single-layer knitted textile layer across the inert material 110, the textile electrodes 130, and the conductive traces 120. In some embodiments, the textile electrodes 130 are knitted as electrical connection regions for a sensor or electronic device affixed to the garment 100.

The textile electrodes 130 can be arranged to, for example, pick up or sense electrical signals from the user's body, such as those related to heart rate and heart function (e.g., the signals for use in forming an electrocardiogram EKG). In some embodiments, the garment 100 includes four textile electrodes 130, positioned with respect to the user's body in order to provide a high-quality EKG signal. The conductive traces 120 connect the textile electrodes 130 to the electrical device 199 via the conductive wires integrated into the hybrid yarn from which the conductive traces 120 are knitted. The conductive wire of the hybrid yarn can be coated with an insulating polymer, which is able to be removed at the points of contact with the textile electrodes 130 and the electrical device 199.

In some embodiments, the hybrid yarn is constructed from a highly inelastic material, such as meta-aramid or para-aramid (e.g., Kevlar® or Twaron®) or a material with similar material properties to protect the integrated conductive wires from damage or being severed during the knitting process and being damaged or severed during normal wear of the garment 100, such as Ultra High Molecular Weight Polyethene (UHMWPE), Polybenzimidazole (PBI), Polyphenylene Benzobisoxazole (PBO), High Strength Polyester, Liquid-Crystal Polymer (LCP), or spider silk. In some embodiments the hybrid yarn is made with a fire retardant and self-extinguishing material, such as para-aramid or material with similar properties according to the ASTM D6413/D6413M Standard Vertical Test Method for Flame Resistance of Textiles to enable the insulating layer and nonconductive yarn to be removed using ablation. The conductive wire can be, for example copper wire or copper-clad stainless-steel sire. Additionally, the textile electrodes 130 may be knitted or otherwise constructed with a conductive wire, such as silver or copper wire or a nonconductive yarn (e.g., nylon, polyester, cotton, or wool) coated with a conductive material such as silver or copper. In some embodiments, the standard material 110, textile electrodes 130, and conductive traces 120 are knitted together into a single-layer garment 100 without seams.

Figure 1B:
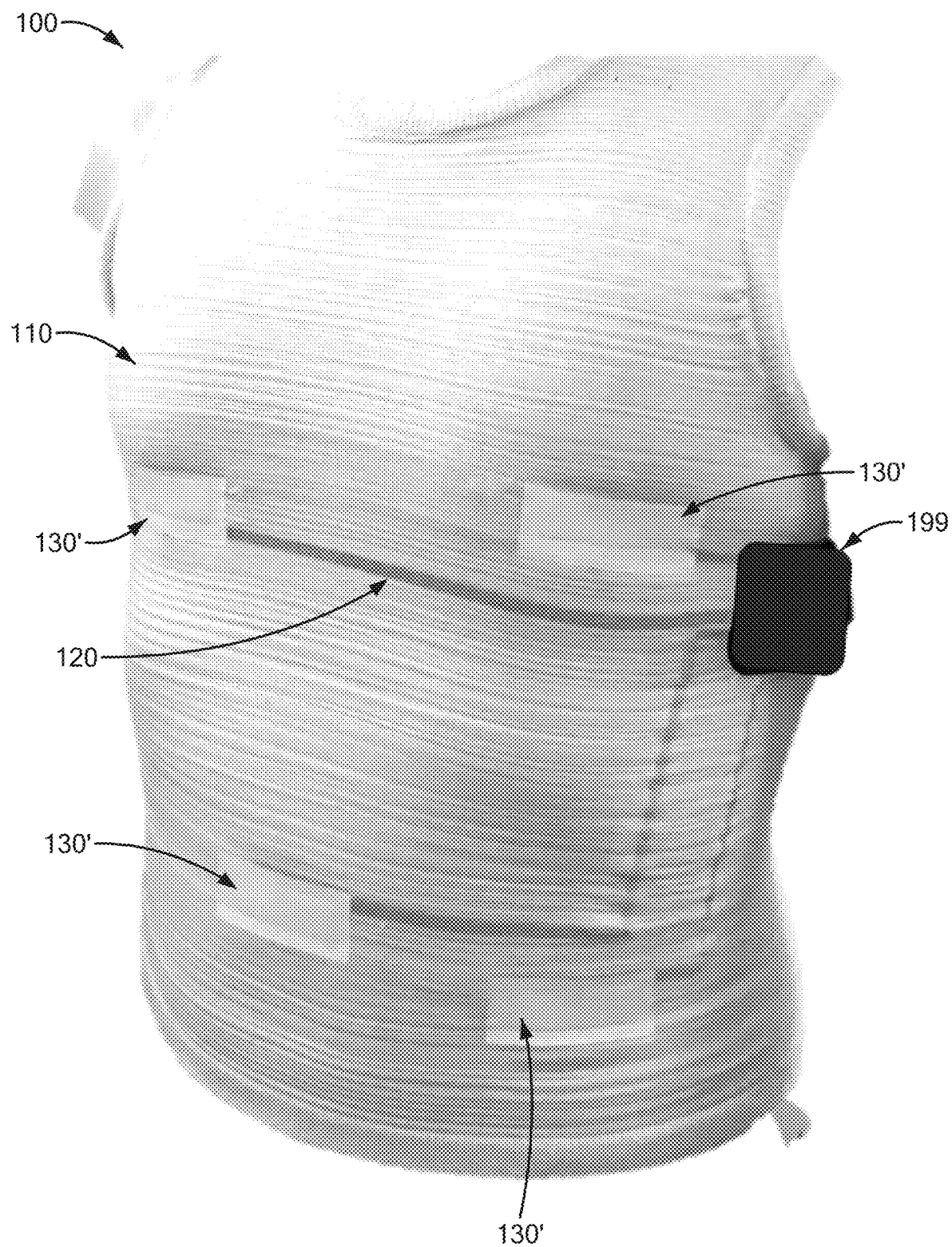
FIG. 1B is a photograph of an illustrative embodiment of the textile of FIG. 1A on a user.

FIG. 1B is a photograph of an illustrative embodiment of the textile of garment 100 FIG. 1A on a user. FIG. 1B shows patches 130' over the textile electrodes 130 that are arranged to maintain a moisture level in the textile electrode 130. These patches 130' can also be used to impart stability to the textile electrode on body when the garment is worn and to reduce electrical static noise from the outer surface of the textile electrode 130.

Examples of a Hybrid Conductive Yarn

Figure 2:
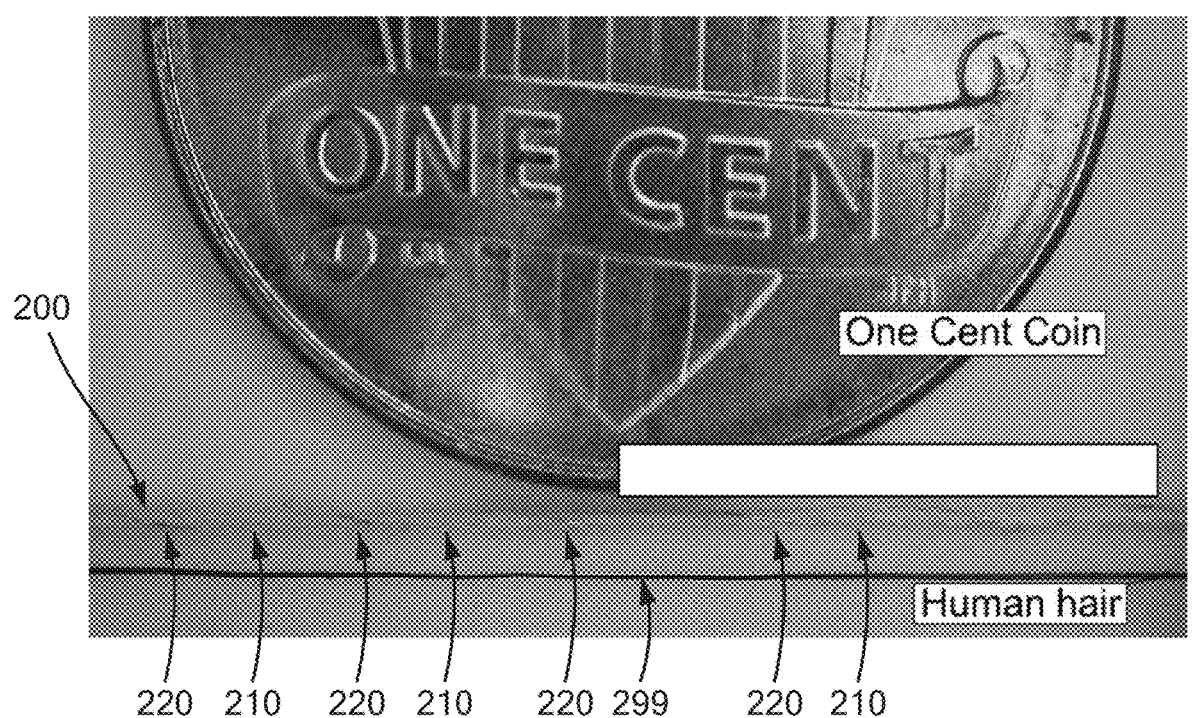
FIG. 2 is a photograph of an illustrative embodiments of a hybrid yarn.

FIG. 2 is a photograph of a strand of a hybrid yarn 200 configured in accordance with illustrative embodiments. To show its relative size, the hybrid yarn 200 is compared with a US penny and a strand of human hair. Preferably, the hybrid yarn 200 is made from a nonconductive yarn 210 and a conductive wire 220 twisted together. In some instances, the nonconductive yarn 210 has minimal elasticity and high strength, and is made from, for example, a meta-aramid or para-aramid material. The nonconductive yarn 210 also can be made from filament or staple fibers. The conductive wire 220 can be insulated with, for example, a polyurethane coating. In some instances, the hybrid yarn 200 can be bonded with a coating (e.g., Nylon) for softer feel and maintain the integrity of the hybrid yarn 200.

In one example, the hybrid yarn 200 includes two stands of copper-clad stainless steel or copper with between 5 to 12 twists per inch around a Kevlar strand. The 5 to 12 twists per inch construction can be a strand of Kevlar and a 50 micron conductive wire (e.g., 43 micron thick metal and a 3-4 micron thick coating of polyurethane) that when twisted together suitable to knit a textile at 15 gauge. The hybrid yarn 200 in FIG. 2 is made from two copper clad stainless-steel wires 220 twisted with a Kevlar yarn 210 at 9 twists per inch. In a final step the hybrid yarn is bonded with Nylon to stabilize the structure and enhance knittability. The yarn resistivity of this embodiment, the making of which is discussed in more detail below, is 17 Ohms/meter. In some instances, other nonconductive yarns 210 can be used, such as Vectran® or Twaron®, which are also a high strength yarns with low elasticity.

Nonconductive yarns 210 made with para aramid or similar materials have many advantages, such as being strong, but relatively light. The specific tensile strength (stretching or pulling strength) of both Kevlar 29 and Kevlar 49 is over eight times greater than that of steel wire. Unlike most plastics it does not melt: it is reasonably good at withstanding temperatures and decomposes only at about 450° C. (850° F.). Accordingly, the hybrid yarn 200 can be laser ablated or burned to remove the nonconductive yarn 210 and the coating on the conductive wire 220.

Figure 3A:
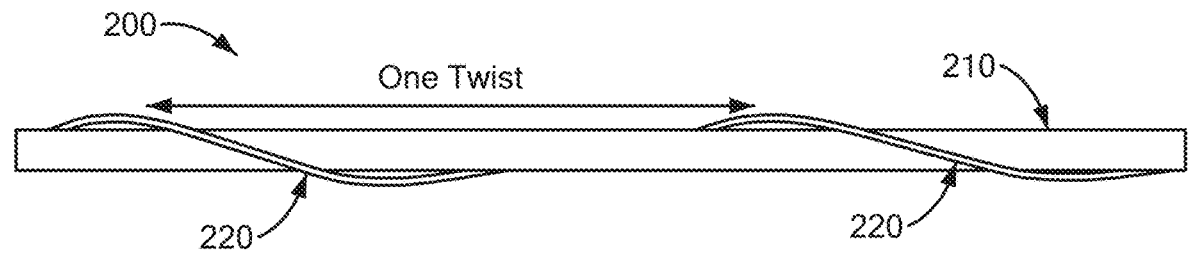
FIGS. 3A-3D are schematic illustrations of example twist patterns of a conductive wire around a nonconductive yarn.

FIG. 3A is a schematic illustration of an example twist pattern of a hybrid yarn 200 having a conductive wire 220 around a nonconductive yarn 210. In order to knit the conductive traces 120 into a single-layer using a flatbed knitting machine the nonconductive yarn 210 must protect conductive wire 220 from being broken by the stresses put on the hybrid yarn 200 by the flatbed knitting machine. According, a hybrid yarn 200 was developed that was suitable for flatbed knitting. The hybrid yarn 200 is constructed from the nonconductive yarn 210 being twisted with the conductive wire 220, where the nonconductive yarn 210 is a strong and inelastic yarn that, when exposed to the tensile forces of the flatbed knitting machine, exhibits an elongation of a sufficiently small percentage to prevent breakage of the conductive wire 220. For example, the nonconductive yarn 210 may have a tensile strength greater than that of the conductive wire 220 as well as an elongation break percentage less than 5 or less than about 4.2. In other embodiments, the nonconductive yarn 210 may have a Young's modulus of 60 or greater. In practice, because the nonconductive yarn 210 and conductive wire 220 are twisted together and the nonconductive yarn 210 comprises the majority fraction of the overall cross-section of the hybrid yarn 200, the material of nonconductive yarn 210 need not simply be less elastic than the metal of conductive wire 220 because, as the hybrid yarn 200 is exposed to tensile forces, the hybrid yarn 200 acts as a single structure and the relative elasticity of the much larger nonconductive yarn 210 section is less than the relative elasticity of the much thinner conductive wire 220 as the hybrid yarn 200 undergoes tension. Accordingly, suitable embodiments of hybrid yarn 200 are constructed from very strong and inelastic fibers, such as meta-aramids and para-aramids, that are both thin and flexible enough to be knitted on a flatbed machine, but also strong and inelastic enough at those thin diameters to be twisted with a substantially thinner metal wire (e.g., a conductive wire 220 thin enough to maintain the thin and flexible properties of the overall hybrid yarn 200 that enable it to be both machine knittable and not affect the worn feeling of a garment) and prevent the substantially thinner metal wire from breaking.

Figure 3B:
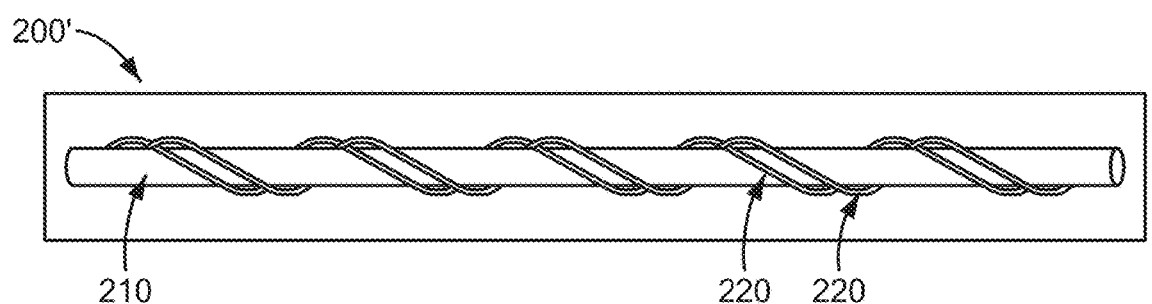
Figure 3C:
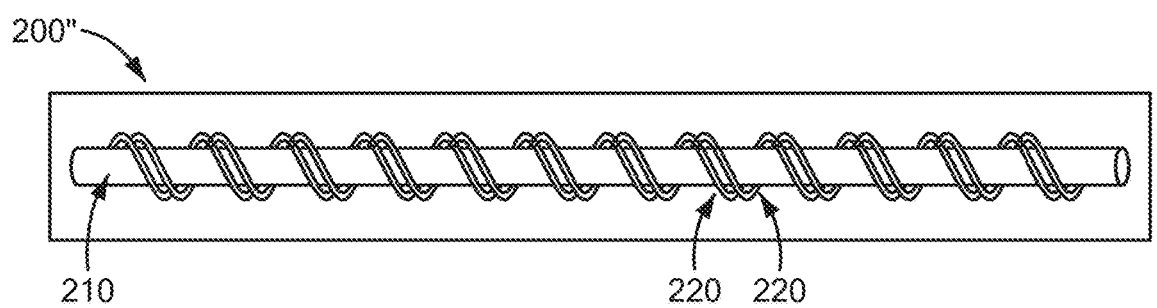
Figure 3D:
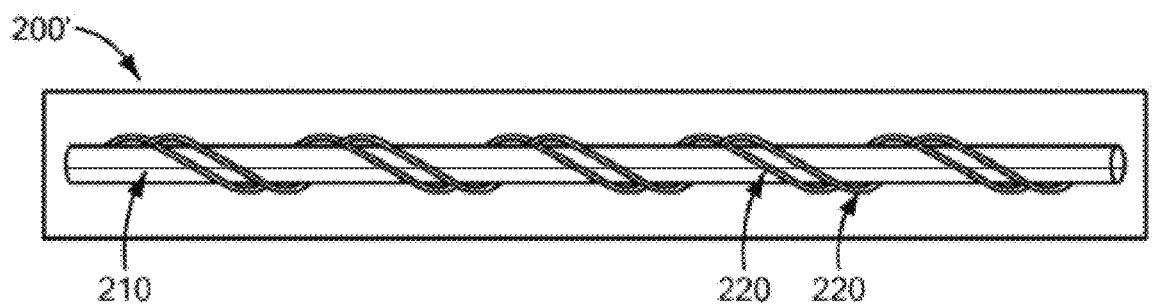

FIG. 3B shows another embodiment of a hybrid conductive yarn 200' having two conductive wires 220 wrapped around a single nonconductive yarn 210 at 5 twists per inch. FIG. 3C shows another embodiment of a hybrid conductive yarn 200" having two conductive wires 220 wrapped around a single nonconductive yarn 210 at 12 twists per inch. FIG. 3D shows another embodiment of a hybrid conductive yarn 200' having two conductive wires 220 wrapped around two non-conductive yarns 210 at 12 twists per inch.

Example Hybrid Conductive Yarn Properties

Nonconductive yarns 210 made with para aramid or similar materials have many advantages, such as being strong, but relatively light. The specific tensile strength (stretching or pulling strength) of both Kevlar 29 and Kevlar 49 is over eight times greater than that of steel wire. Unlike most plastics it does not melt: it is reasonably good at withstanding temperatures and decomposes only at about 450° C. (850° F.). Similarly, Aramid fibers can be used for the nonconductive yarn 210. Aramid fibers are created with a range of beneficial properties, and come in two types, para-aramid and meta-aramid, both of which are suitable. Kevlar is an example of a para-aramid fiber. These generally have a high strength-to-weight ratio and great tenacity, making them abrasion-resistant. Other advantages include:

High Young's Modulus (i.e., structural rigidity, also known as "elastic modulus," which defines the relationship between stress and strain in a material) of, for example 60 to 179 GPa.

Low elongation at break point (i.e., the yarn stretches very little under tension).

Nonconductive under normal conditions.

Resistance to abrasion and cutting.

Resistance to organic solvents.

Retain low flammability, resistant to thermal degradation, and self-extinguishing.

Keep fabric integrity at elevated temperatures.

Excellent dimensional stability.

TABLE 1

| Material | Strength-to-weight KN · m/kg. | Ultimate Tensile Strength MPa | Density g/cm3 |
| --- | --- | --- | --- |
| Kevlar | 2514 | 2757 | 1.44 |
| Carbon Fiber | 2457 | 4137 | 1.75 |
| E Glass Fiber | 1307 | 3450 | 2.57 |
| Carbon Laminate | 785 | 1600 | 1.5 |
| E Glass Laminate | 775 | 1500 | 1.97 |
| Nylon | 69 | 75 | 1.15 |

TABLE 2

| Material | Young's Modulus GPa |
| --- | --- |
| Aramid (such as Kevlar and Twaron) | 70.5-112.4 |
| Nylon | 2-4 |
| Polypropylene | 1.5-2 |

Meta-aramid fibers are another example of a suitable nonconductive yarn 210 for use in the hybrid yarn 200 and they have the following advantages:

Heat resistance: Meta-aramid has long-lasting thermal stability. It can operate for long time at a temperature of 204° C. and it maintains excellent dimensional stability. It is not overly brittle, and does not soften or melt even if it is briefly exposed to temperatures up to about 300° C.

Flame resistance: Meta-aramid is inherently flame resistant. It does not self-burn or melt at regular levels of oxygen. It is self-extinguishing and should carbonize at 400° C.

Electrical insulation: Meta-aramid has excellent electrical insulation properties. The dielectric strength of meta-aramid paper is up to about 20 kv/mm, but varies depending on the particular meta-aramid.

Chemical stability: Meta-aramid has a very stable chemical structure and is resistant to organic solvents.

Radiation resistance: Good resistance to Ultraviolet, α (alpha) and β (beta).

Mechanical properties: Meta-aramid is formable for moldable parts.

Low elongation at break point as well as para-aramid (i.e., it exhibits a minimal stretch under tension).

While helpful properties of para-aramid and meta-aramid have been listed above, Table 3 shows the various characteristics of aramid fibers compiled from the Chemical Economics Handbook and Encyclopedia of Chemical Technology, Vol. 19 and Indian Journal of Fiber and Textile Research.

TABLE 3

Properties of Commercial Aramid Fibers

| Fiber Type | Density g/cm3 | Extension to Break % | Modulus GPa | Loop Elongation % |
| --- | --- | --- | --- | --- |
| Kevlar29 | 1.43 | 3.6 | 70 | 2.1 |
| Kevlar49 | 1.45 | 2.8 | 135 | 1.3 |
| Kevlar119 | 1.44 | 4.4 | 55 | 2.7 |
| Kevlar129 | 1.45 | 3.3 | 99 | |
| Kevlar149 | 1.47 | 1.5 | 143 | 0.6 |
| Nomex | 1.38 | 22 | 17 | |
| Twaron | 1.44 | 3.3 | 79 | |
| Twaron HM | N/a | 2 | 123 | |
| Technora | 1.39 | 4.3 | 70 | |
| Technora V106 | 1.32 | 3.7 | 77 | |

Example Hybrid Conductive Yarn Advantages

Existing commercial hybrid yarns often incorporate stretch core such as Spandex and a metal wire wrapped around it. When this type of yarn is fed through a knitting machine with tension applied the yarn stretches and appears smooth. However, when the yarn relaxes after the knitting process is complete and goes back to its original length, the wire randomly retracts and potentially kinks. Kinking subsequently can lead to breakage or malfunction, resulting in a failed electrical circuit. As discussed above, hybrid yarns of the present disclosure are stable with little to no elongation and protects the wires during a machine the knitting process. Low elasticity and high tensile strength materials, such as para-aramid yarn, keeps the twisted conductive wires 220 from overstretching or breaking. Additionally, within the knit structure the nonconductive yarn 210 examples disclosed herein also protect the conductive wire 220 from daily wear and tear due to their high tensile strength.

Because the conductive wires 220 wires are insulated and continuous, power flow is contained throughout the region or structure knitting using the hybrid yarn. This contrasts with most known processes in which e-traces are uninsulated and are later protected by application of external materials such as films etc. This is an additive process. Embodiments of the present disclosure can involve knitting in an integrated method yielding a single textile layer only, without needing to add a conductive layer, film or coating overtop the trace regions. These additional materials not only add additional manufacturing steps, it also adds bulk, rigidity and opportunity for failure.

Finally, if or when a connection needs to be made to the conductive trace region 120, the hybrid yarn 200 can be ablated at any point chosen to expose the conductive wire 220. In an example process of ablation, nonconductive yarn 210 made using a Para-aramid material and a polymer insulation layer on the conductive wire 220 burns or vaporizes off, leaving access to the metal surface. Embodiments include nonconductive yarn 210 made with self-extinguishing fibers, such as para-aramids, and any ablation is strictly contained to a target area.

Examples of Manufacturing a Hybrid Conductive Yarn

Figure 4E:
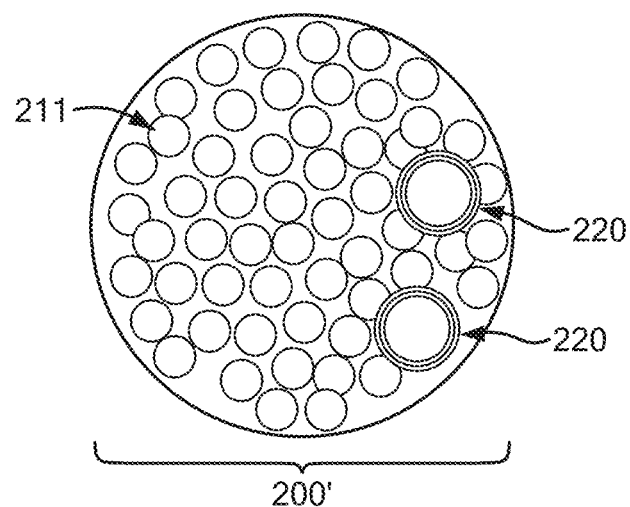
Figure 4F:
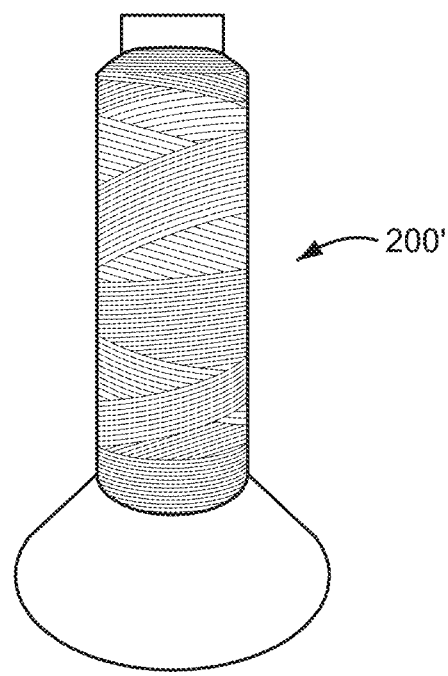

FIGS. 4A-4F are schematic illustration of an example construction steps for making an example hybrid yarn 200. FIG. 4A shows bare conductive wire 220' including a copper exterior layer 223 and a solid stainless-steel core 221. The bare conductive wire 220' can be between 10 and 100 microns thick, which is thin and flexible enough to be integrated into the yarn of a knitted textile without affecting the performance of the carrier fabric (e.g., the nonconductive yarn 210), but thick enough to be durable and carry sufficient power and data at desired noise levels. In FIG. 4B, the conductive wire 220 is formed by adding a layer of insulating material (e.g., polyurethane or similar). The layer insulating material could be, for example, between 1 and 10 microns thick and rated to 300° F. In FIG. 4C a bundle of staple fibers 211, which together form the nonconductive yarn 210 are brought together, and, in some instances, twisted together. For example, the staple fibers 211 could be Kevlar® or Twaron® of 350-400 Denier. In FIG. 4D, the staple fibers 211 and/or the nonconductive yarn 210 is twisted together with the conductive wires 220 between 1 and 15 twists per inch. In FIG. 4E, the hybrid yarn 200 is coated with a polymer, such as Nylon (or similar polymer) in a bonding step to give a soft feel to the final treated hybrid yarn 200' with, for example a final Denier of about 800 D. In a final step, show in FIG. 4F, the treated hybrid yarn 200' is wound into a cone and ready to be fed into a flatbed knitting machine.

Figure 5:
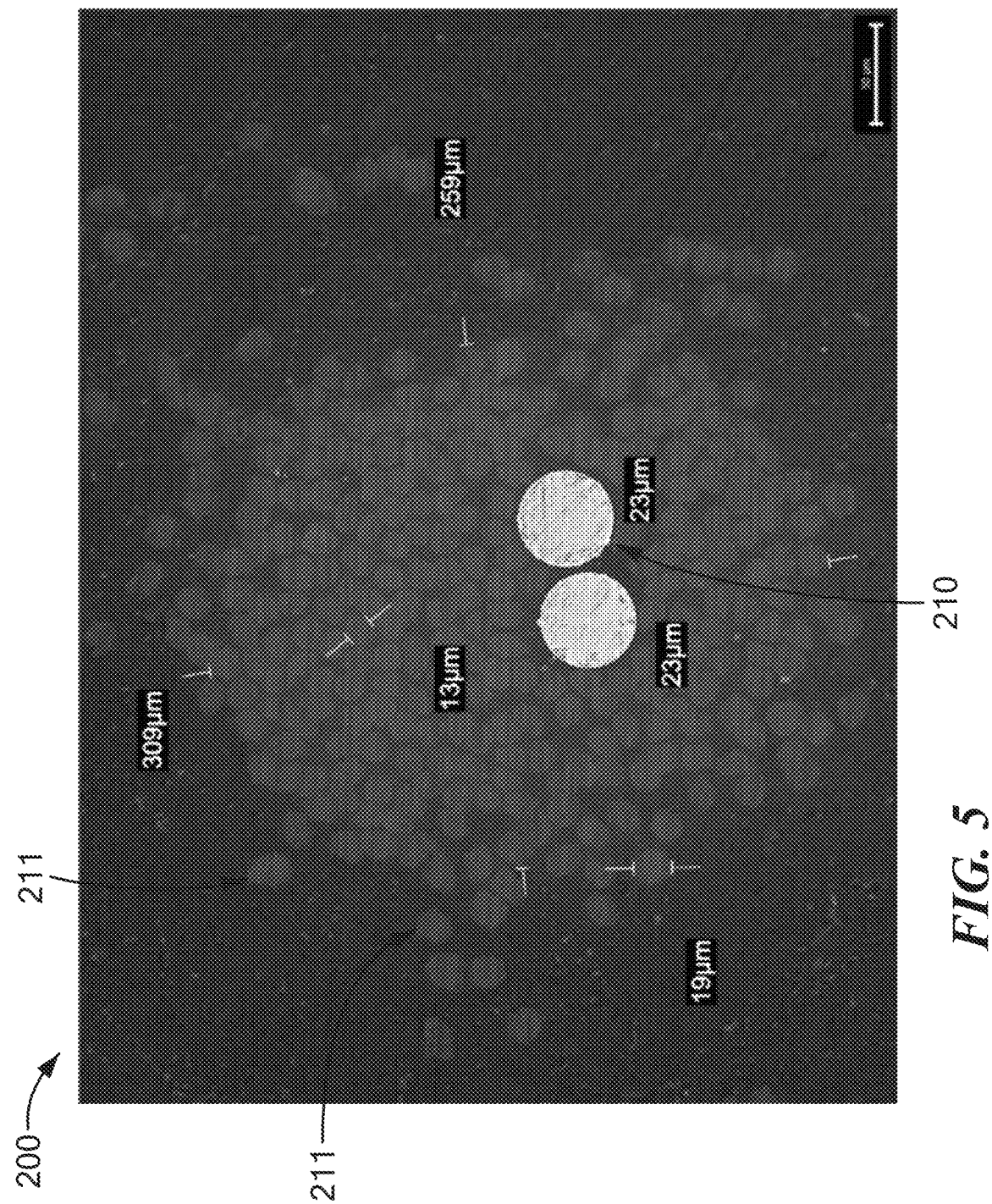
FIG. 5 is a microscope photograph of a cross-sectional view of an example hybrid yarn.

FIG. 5 is a microscope photograph of a cross-sectional view of an example hybrid yarn bonded with nylon. FIG. 5 shows the staple fibers 211 of about 13 to 19 microns in diameters twisted with two conductive wires 220 of about 23 microns in diameter, with the overall hybrid yarn having between 259 and 309 microns of thickness at the core bundle.

Example Knitted Textile Constructs using Hybrid Conductive Yarn

Figure 6A:
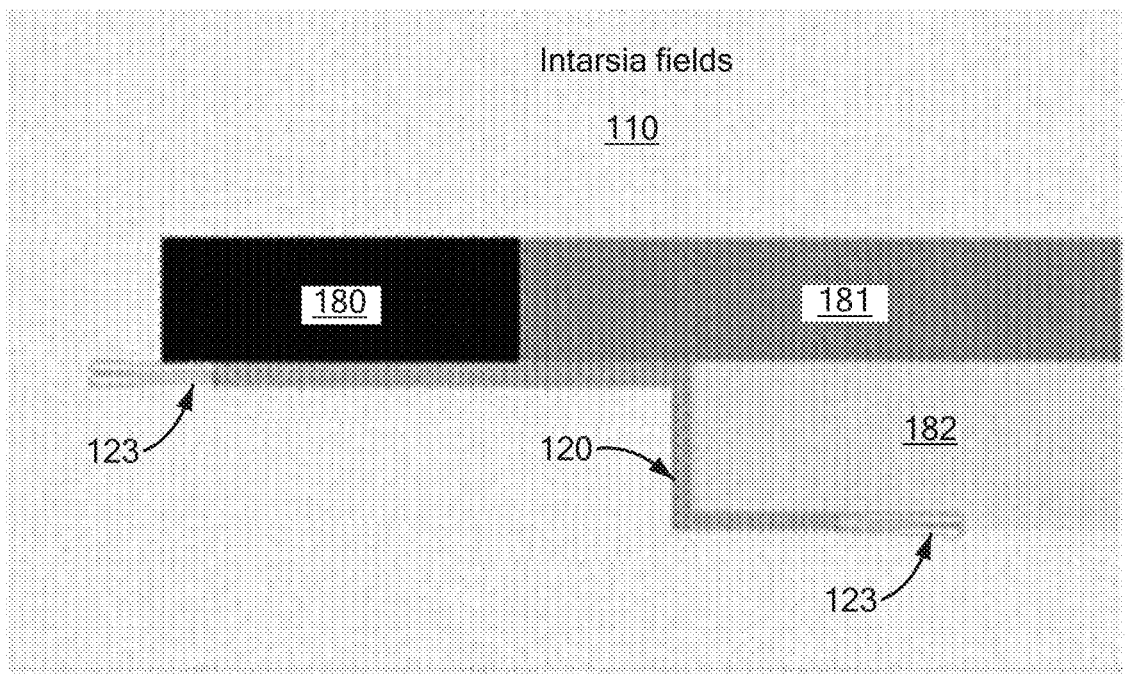
FIG. 6A is a photograph of a continuous textile section knitted using the intarsia technique and having a conductive trace region passing through a plurality of distinct regions of the textile section.

FIG. 6A is a photograph of a continuous textile section knitted using the intarsia technique and having a conductive trace region passing through a plurality of distinct regions of the textile section. FIG. 6A shows multiple different yarns knitted into a single textile using the intarsia technique. FIG. 6A shows a conductive trace 120 knitted between a standard material 110 by way of knitting individual regions 180, 181, 182 around the conductive trace 120 in the standard material 110 to form the bends of the conductive trace 120. In some embodiments, the individual regions 180, 181, 182 are knitted from the standard material 110, and one or more of them could also be made from a different material, such as a conductive thread to form a textile electrode 130 in contact with the conductive trace 120.

Figure 6B:
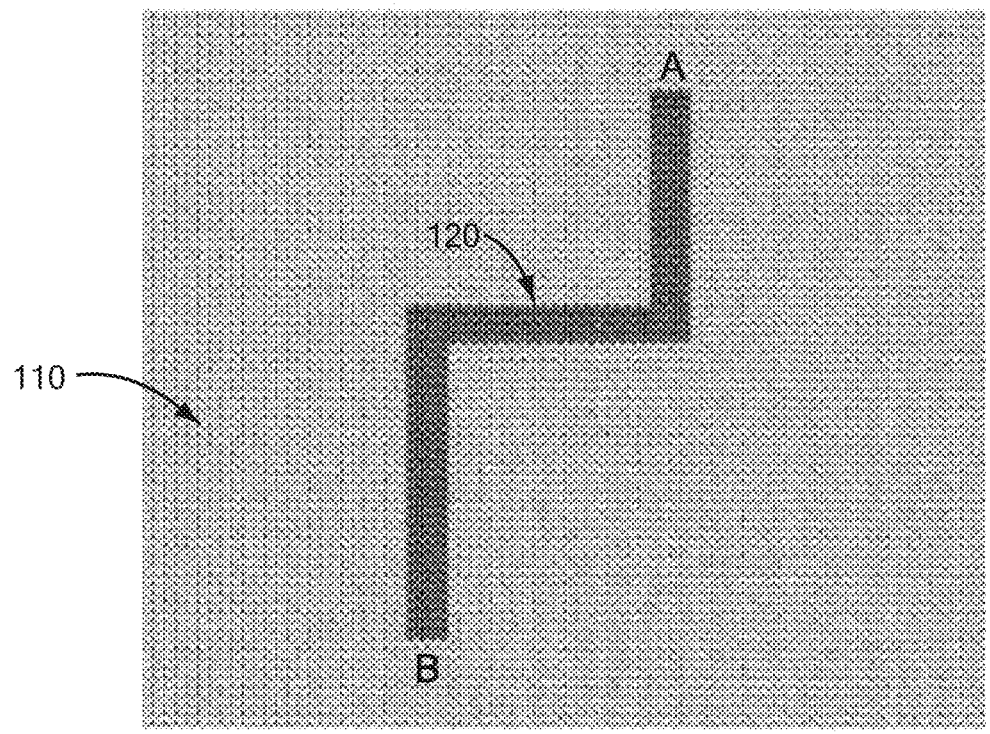
FIG. 6B is a photograph of a continuous textile section knitted using the intarsia technique and having a conductive trace region passing through an inert region from a first location to a second location.

FIG. 6B is a photograph of a continuous textile section knitted using the intarsia technique and having a conductive trace region passing through an inert region from a first location to a second location. FIG. 6B is an example of the multi-region knitting of FIG. 6A, where all the regions 180, 181, 182 were knitted from the same material as the rest of the garment outside of the conductive trace 120 (i.e., the inert yarn 111). FIG. 6B shows a hybrid yarn knitted into a conductive trace 120 in an inert region 110 of a continuous textile section that change direction and provides an electrical connection between a first location (A) and a second location (B). This can, for example, enables the control device 199 of FIG. 1A to be connected to the conductive trace 120 at location (A) and provide an electrical connection to a textile electrode 130 at location (B) via the conductive wires 220 in the conductive trace 120 that extend continuously between (A) to (B).

Figure 7A:
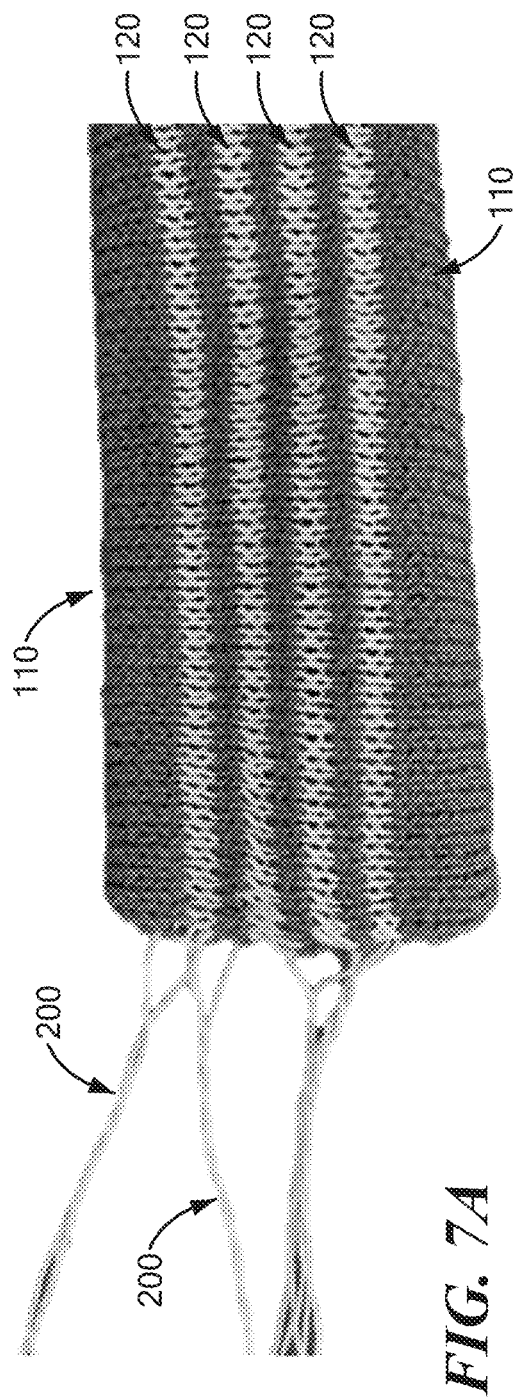
FIG. 7A is a photograph of an illustrative embodiment of a knitted textile having conductive traces with loose ends of hybrid yarn extending from the conductive traces.
Figure 7B:
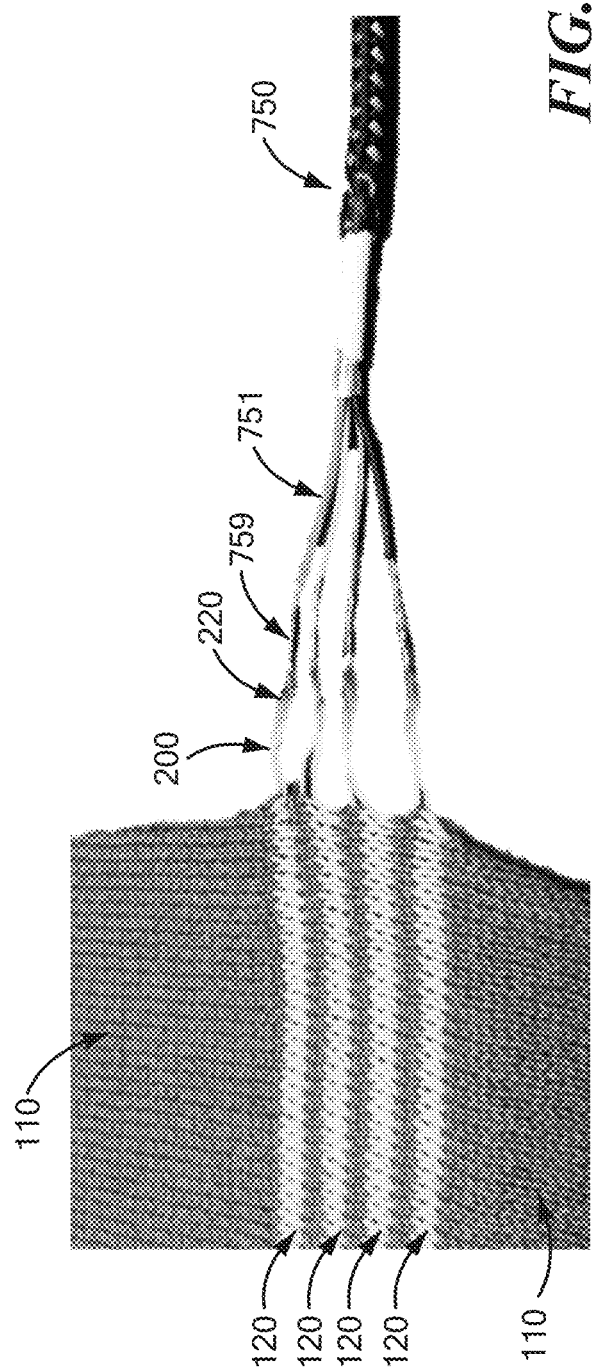
FIG. 7B is a photograph of the knitted textile of FIG. 7A with the loose ends having their conductive wires soldered to a corresponding copper wire of a wire assembly.

FIG. 7A is a photograph of an embodiment of a knitted textile having conductive traces 120 with loose ends of hybrid yarn 200 extending from each of the conductive traces 120 and FIG. 7B is a photograph of the knitted textile of FIG. 7A with the loose ends having their conductive wires 220 soldered 759 to a corresponding copper wire 751 of a wire assembly 750.

Figure 8:
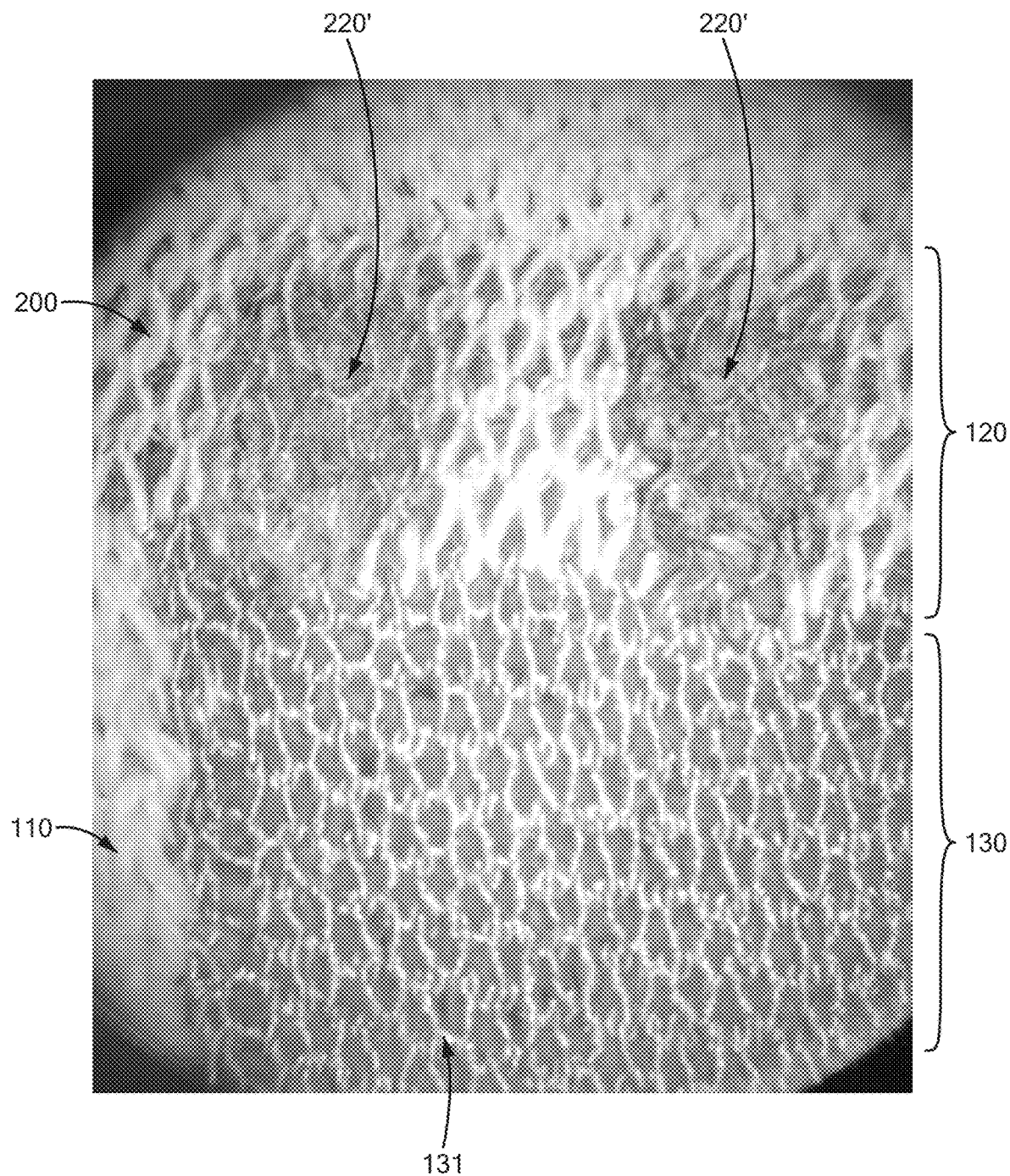
FIG. 8 is a photograph of a textile section with a conductive trace region of hybrid yarn and an electrode region showing an ablated region of the hybrid yarn.

FIG. 8 is a photograph of a conductive trace region 120 adjacent to a textile electrode region 130 with a portion of the nonconductive fibers 210 of the hybrid yarn 200 of the conductive trace region having been removed using ablation to expose uninsulated portions 220' of the conductive wire, where the ablation also removed the coating on a polymer conductive wire 220.

The embodiments of the invention described above are intended to be merely exemplary; numerous variations and modifications will be apparent to those skilled in the art. One skilled in the art will appreciate further features and advantages of the disclosure based on the above-described embodiments. Such variations and modifications are intended to be within the scope of the present invention as defined by any of the appended claims. Accordingly, the disclosure is not to be limited by what has been particularly shown and described, except as indicated by the appended claims. All publications and references cited herein are expressly incorporated herein by reference in their entirety.

What is claimed is:

1. A machine-knittable hybrid yarn, comprising:
   one or more electrically non-conductive yarns;
   two or more electrically conductive wires wrapped around the electrically non-conductive yarns, the electrically conductive wires having an exterior layer of an insulating material,
   wherein the number of electrically non-conductive yarns is less than the number of electrically conductive wires;
   wherein the electrically non-conductive yarns comprise a majority fraction of an overall cross-section of the hybrid yarn; and wherein the two or more electrically conductive wires are wrapped around the one or more electrically non-conductive yarns at between 1 and 15 twists per inch,
wherein the one or more electrically non-conductive yarns are 1500 denier or finer.

2. The hybrid yarn of claim 1, wherein the two or more electrically conductive wires are wrapped around the one or more electrically non-conductive yarns with Z twist or an S twist from a single twisting process.

3. The hybrid yarn of claim 1,
wherein the two or more electrically conductive wires are wrapped around the one or more electrically non-conductive yarns at between 5 and 12 twists per inch.

4. The hybrid yarn of claim 1, wherein the two or more electrically conductive wires define a continuous strand of metal along the hybrid yarn.

5. The hybrid yarn of claim 1, wherein the hybrid yarn is bonded with a polymer layer.

6. The hybrid yarn of claim 5, wherein the hybrid yarn is bonded with Nylon.

7. The hybrid yarn of claim 1, wherein the insulating material of the two or more electrically conductive wires comprises a polymer coating.

8. The hybrid yarn of claim 1, wherein the two or more electrically conductive wires are approximately 10 to 100 microns thick.

9. The hybrid yarn of claim 1, wherein the one or more electrically non-conductive yarns have an elasticity less than that of the wrapped two or more electrically conductive wires such that the two or more electrically conductive wires do not break before the one or more electrically non-conductive yarns under tensile loading of the hybrid yarn.

10. The hybrid yarn of claim 1, wherein the one or more electrically non-conductive yarns are fire retardant and self-extinguishing.

11. The hybrid yarn of claim 1, wherein the one or more electrically non-conductive yarns are no-melt and no-drip according to the ASTM D6413/D6413M Standard Vertical Test Method for Flame Resistance of Textiles.

12. The hybrid yarn of claim 1, wherein the one or more electrically non-conductive yarns have a tensile strength higher than the two or more electrically conductive wires.

13. The hybrid yarn of claim 1,
wherein the one or more electrically non-conductive yarns have a Young's modulus of at least 60 GPa.

14. The hybrid yarn of claim 1, wherein the one or more electrically non-conductive yarns comprise at least one of an aramid, meta-aramid, or para-aramid polyamide fiber.

15. The hybrid yarn of claim 1, wherein the one or more electrically non-conductive yarns comprise at least one: Ultra High Molecular Weight Polyethene (UHMWPE), Polybenzimidazole (PBI), Polyphenylene Benzobisoxazole (PBO), High Strength Polyester, Liquid-Crystal Polymer (LCP), or spider silk.

16. The hybrid yarn of claim 1, wherein the two or more electrically conductive wires comprise a copper-clad stainless steel wire or a solid copper wire.

17. The hybrid yarn of claim 1,
wherein the one or more electrically non-conductive yarns and the insulating material each have a decomposition temperature greater than a melting point of the two or more electrically conductive wires.

18. The hybrid yarn of claim 1, wherein the one or more electrically non-conductive yarns comprise staple fibers.

19. The hybrid yarn of claim 1,
wherein the two or more electrically conductive wires are a first two electrically conductive wires, and the hybrid yarn further comprises a third electrically conductive wire wrapped with the one or more electrically non-conductive yarns.

20. A machine-knittable hybrid yarn, comprising:
one or more electrically non-conductive yarns; and
two or more electrically conductive wires wrapped around the one or more electrically non-conductive yarns, the two or more electrically conductive wires having an exterior layer of an insulating material,
wherein the one or more electrically non-conductive yarns have a tensile strength higher than a tensile strength of the two or more electrically conductive wires,
wherein the number of electrically non-conductive yarns is less than the number of electrically conductive wires;
wherein the one or more electrically non-conductive yarns comprise a majority fraction of an overall cross-section of the hybrid yarn; and
wherein the one or more electrically non-conductive yarns are fire retardant and self-extinguishing.

21. A method of making a machine-knittable hybrid yarn, the method comprising:
wrapping, in a single process, two or more electrically conductive wires around one or more electrically non-conductive yarns, the electrically conductive wires each having an exterior coated with an insulating material,
wherein the number of electrically non-conductive yarns is less than the number of electrically conductive wires;
wherein the electrically non-conductive yarns comprise a majority fraction of an overall cross-section of the hybrid yarn, and
wherein the one or more electrically non-conductive yarns comprise at least one: Ultra High Molecular Weight Polyethene (UHMWPE), Polybenzimidazole (PBI), Polyphenylene Benzobisoxazole (PBO), High Strength Polyester, Liquid-Crystal Polymer (LCP), or spider silk.

22. The method of claim 21, further comprising:
bonding, after the wrapping, the wrapped one or more electrically non-conductive yarns and the two or more electrically conductive wires with an electrically non-conductive exterior layer.

23. The method of claim 22,
wherein the one or more electrically non-conductive later yarns comprises a polymer.

24. The method of claim 21,
wherein the two or more electrically conductive wires are wrapped around the one or more electrically non-conductive yarns at between 1 and 15 twists per inch.

25. The method of claim 21, wherein the one or more electrically non-conductive yarns have an elasticity less than that of the wrapped two or more electrically conductive wires such that the two or more electrically conductive wires do not break before the one or more electrically non-conductive yarns under tensile loading of the hybrid yarn.

26. The method of claim 21, wherein the one or more electrically non-conductive yarns are fire retardant and self-extinguishing.

27. The method of claim 21, wherein the one or more electrically non-conductive yarns have a tensile strength higher than the two or more electrically conductive wires.

28. The method of claim 21,
wherein the one or more electrically non-conductive yarns have a Young's modulus of at least 60 GPa.

29. The method of claim 21,
wherein the one or more electrically non-conductive yarns have a break elongation percentage of 4.2 or less.

30. The method of claim 21, wherein the one or more electrically non-conductive yarns further comprise at least one of: an aramid, meta-aramid, or para-aramid polyamide fiber.

31. The method of claim 21, wherein the two or more electrically conductive wires comprise a copper-clad stainless steel wire or a solid copper wire.

32. The method of claim 21, wherein the one or more electrically non-conductive yarns comprise staple fibers.

33. The hybrid yarn of claim 20, wherein the one or more electrically non-conductive yarns have a break elongation percentage of 4.2 or less.

34. The hybrid yarn of claim 20, wherein the one or more electrically non-conductive yarns are 1500 denier or finer.

35. The hybrid yarn of claim 20, wherein the one or more electrically non-conductive yarns are no-melt and no-drip according to the ASTM D6413/D6413M Standard Vertical Test Method for Flame Resistance of Textiles.

36. The hybrid yarn of claim 20, wherein the one or more electrically non-conductive yarns comprise at least one of an aramid, meta-aramid, or para-aramid polyamide fiber.

37. The hybrid yarn of claim 20, wherein the one or more electrically non-conductive yarns and the insulating material each have a decomposition temperature greater than a melting point of the two or more electrically conductive wires.

38. The hybrid yarn of claim 20, wherein the one or more electrically non-conductive yarns comprise staple fibers.

39. A machine-knittable hybrid yarn, comprising:
one or more electrically non-conductive yarns;
two or more electrically conductive wires wrapped around the electrically non-conductive yarns, the electrically conductive wires having an exterior layer of an insulating material,
wherein the number of electrically non-conductive yarns is less than the number of electrically conductive wires;
wherein the electrically non-conductive yarns comprise a majority fraction of an overall cross-section of the hybrid yarn;
wherein the two or more electrically conductive wires are wrapped around the one or more electrically non-conductive yarns at between 1 and 15 twists per inch; and
wherein the one or more electrically non-conductive yarns have an elasticity less than that of the wrapped two or more electrically conductive wires such that the two or more electrically conductive wires do not break before the one or more electrically non-conductive yarns under tensile loading of the hybrid yarn.

40. The hybrid yarn of claim 39, wherein the one or more electrically non-conductive yarns are 1500 denier or finer.

41. The hybrid yarn of claim 39, wherein the one or more electrically non-conductive yarns are fire retardant and self-extinguishing.

42. The hybrid yarn of claim 39, wherein the one or more electrically non-conductive yarns are no-melt and no-drip according to the ASTM D6413/D6413M Standard Vertical Test Method for Flame Resistance of Textiles.

43. The hybrid yarn of claim 39, wherein the one or more electrically non-conductive yarns have a tensile strength higher than the two or more electrically conductive wires.

44. The hybrid yarn of claim 39, wherein the one or more electrically non-conductive yarns comprise staple fibers.

45. A machine-knittable hybrid yarn, comprising:
one or more electrically non-conductive yarns;
two or more electrically conductive wires wrapped around the electrically non-conductive yarns, the electrically conductive wires having an exterior layer of an insulating material,
wherein the number of electrically non-conductive yarns is less than the number of electrically conductive wires;
wherein the electrically non-conductive yarns comprise a majority fraction of an overall cross-section of the hybrid yarn;
wherein the two or more electrically conductive wires are wrapped around the one or more electrically non-conductive yarns at between 1 and 15 twists per inch, and
wherein the one or more electrically non-conductive yarns are fire retardant and self-extinguishing.

46. The hybrid yarn of claim 45, wherein the one or more electrically non-conductive yarns are 1500 denier or finer.

47. The hybrid yarn of claim 45, wherein the one or more electrically non-conductive yarns have an elasticity less than that of the wrapped two or more electrically conductive wires such that the two or more electrically conductive wires do not break before the one or more electrically non-conductive yarns under tensile loading of the hybrid yarn.

48. The hybrid yarn of claim 45, wherein the one or more electrically non-conductive yarns are no-melt and no-drip according to the ASTM D6413/D6413M Standard Vertical Test Method for Flame Resistance of Textiles.

49. The hybrid yarn of claim 45, wherein the one or more electrically non-conductive yarns have a tensile strength higher than the two or more electrically conductive wires.

50. The hybrid yarn of claim 45, wherein the one or more electrically non-conductive yarns comprise staple fibers.

51. A machine-knittable hybrid yarn, comprising:
one or more electrically non-conductive yarns;
two or more electrically conductive wires wrapped around the electrically non-conductive yarns, the electrically conductive wires having an exterior layer of an insulating material,
wherein the number of electrically non-conductive yarns is less than the number of electrically conductive wires;
wherein the electrically non-conductive yarns comprise a majority fraction of an overall cross-section of the hybrid yarn;
wherein the two or more electrically conductive wires are wrapped around the one or more electrically non-conductive yarns at between 1 and 15 twists per inch, and
wherein the one or more electrically non-conductive yarns are no-melt and no-drip according to the ASTM D6413/D6413M Standard Vertical Test Method for Flame Resistance of Textiles.

52. The hybrid yarn of claim 51, wherein the one or more electrically non-conductive yarns are 1500 denier or finer.

53. The hybrid yarn of claim 51, wherein the one or more electrically non-conductive yarns have an elasticity less than that of the wrapped two or more electrically conductive wires such that the two or more electrically conductive wires do not break before the one or more electrically non-conductive yarns under tensile loading of the hybrid yarn.

54. The hybrid yarn of claim 51, wherein the one or more electrically non-conductive yarns are fire retardant and self-extinguishing.

55. The hybrid yarn of claim 51, wherein the one or more electrically non-conductive yarns have a tensile strength higher than the two or more electrically conductive wires.

56. The hybrid yarn of claim 51, wherein the one or more electrically non-conductive yarns comprise staple fibers.

57. A machine-knittable hybrid yarn, comprising:
one or more electrically non-conductive yarns;
two or more electrically conductive wires wrapped around the electrically non-conductive yarns, the electrically conductive wires having an exterior layer of an insulating material,
wherein the number of electrically non-conductive yarns is less than the number of electrically conductive wires;
wherein the electrically non-conductive yarns comprise a majority fraction of an overall cross-section of the hybrid yarn;
wherein the two or more electrically conductive wires are wrapped around the one or more electrically non-conductive yarns at between 1 and 15 twists per inch, and
wherein the one or more electrically non-conductive yarns have a tensile strength higher than the two or more electrically conductive wires.

58. The hybrid yarn of claim 57, wherein the one or more electrically non-conductive yarns are 1500 denier or finer.

59. The hybrid yarn of claim 57, wherein the one or more electrically non-conductive yarns have an elasticity less than that of the wrapped two or more electrically conductive wires such that the two or more electrically conductive wires do not break before the one or more electrically non-conductive yarns under tensile loading of the hybrid yarn.

60. The hybrid yarn of claim 57, wherein the one or more electrically non-conductive yarns are fire retardant and self-extinguishing.

61. The hybrid yarn of claim 57, wherein the one or more electrically non-conductive yarns are no-melt and no-drip according to the ASTM D6413/D6413M Standard Vertical Test Method for Flame Resistance of Textiles.

62. The hybrid yarn of claim 57, wherein the one or more electrically non-conductive yarns comprise staple fibers.

63. A machine-knittable hybrid yarn, comprising:
one or more electrically non-conductive yarns;
two or more electrically conductive wires wrapped around the electrically non-conductive yarns, the electrically conductive wires having an exterior layer of an insulating material,
wherein the number of electrically non-conductive yarns is less than the number of electrically conductive wires;
wherein the electrically non-conductive yarns comprise a majority fraction of an overall cross-section of the hybrid yarn;
wherein the two or more electrically conductive wires are wrapped around the one or more electrically non-conductive yarns at between 1 and 15 twists per inch, and
wherein the one or more electrically non-conductive yarns comprise at least one of an aramid, meta-aramid, or para-aramid polyamide fiber.

64. The hybrid yarn of claim 63, wherein the one or more electrically non-conductive yarns are 1500 denier or finer.

65. The hybrid yarn of claim 63, wherein the one or more electrically non-conductive yarns have an elasticity less than that of the wrapped two or more electrically conductive wires such that the two or more electrically conductive wires do not break before the one or more electrically non-conductive yarns under tensile loading of the hybrid yarn.

66. The hybrid yarn of claim 63, wherein the one or more electrically non-conductive yarns are fire retardant and self-extinguishing.

67. The hybrid yarn of claim 63, wherein the one or more electrically non-conductive yarns are no-melt and no-drip according to the ASTM D6413/D6413M Standard Vertical Test Method for Flame Resistance of Textiles.

68. The hybrid yarn of claim 63, wherein the one or more electrically non-conductive yarns have a tensile strength higher than the two or more electrically conductive wires.

69. The hybrid yarn of claim 63, wherein the one or more electrically non-conductive yarns comprise staple fibers.

70. A machine-knittable hybrid yarn, comprising:
one or more electrically non-conductive yarns;
two or more electrically conductive wires wrapped around the electrically non-conductive yarns, the electrically conductive wires having an exterior layer of an insulating material,
wherein the number of electrically non-conductive yarns is less than the number of electrically conductive wires;
wherein the electrically non-conductive yarns comprise a majority fraction of an overall cross-section of the hybrid yarn;
wherein the two or more electrically conductive wires are wrapped around the one or more electrically non-conductive yarns at between 1 and 15 twists per inch, and
wherein the one or more electrically non-conductive yarns and the insulating material each have a decomposition temperature greater than a melting point of the two or more electrically conductive wires.

71. The hybrid yarn of claim 70, wherein the one or more electrically non-conductive yarns are 1500 denier or finer.

72. The hybrid yarn of claim 70, wherein the one or more electrically non-conductive yarns have an elasticity less than that of the wrapped two or more electrically conductive wires such that the two or more electrically conductive wires do not break before the one or more electrically non-conductive yarns under tensile loading of the hybrid yarn.

73. The hybrid yarn of claim 70, wherein the one or more electrically non-conductive yarns are fire retardant and self-extinguishing.

74. The hybrid yarn of claim 70, wherein the one or more electrically non-conductive yarns are no-melt and no-drip according to the ASTM D6413/D6413M Standard Vertical Test Method for Flame Resistance of Textiles.

75. The hybrid yarn of claim 70, wherein the one or more electrically non-conductive yarns have a tensile strength higher than the two or more electrically conductive wires.

76. The hybrid yarn of claim 70, wherein the one or more electrically non-conductive yarns comprise staple fibers.

77. A machine-knittable hybrid yarn, comprising:
one or more electrically non-conductive yarns;
two or more electrically conductive wires wrapped around the electrically non-conductive yarns, the electrically conductive wires having an exterior layer of an insulating material,
wherein the number of electrically non-conductive yarns is less than the number of electrically conductive wires;
wherein the electrically non-conductive yarns comprise a majority fraction of an overall cross-section of the hybrid yarn;
wherein the two or more electrically conductive wires are wrapped around the one or more electrically non-conductive yarns at between 1 and 15 twists per inch, and
wherein the one or more electrically non-conductive yarns comprise staple fibers.

78. The hybrid yarn of claim 77, wherein the one or more electrically non-conductive yarns are 1500 denier or finer.

79. The hybrid yarn of claim 77, wherein the one or more electrically non-conductive yarns are fire retardant and self-extinguishing.

80. The hybrid yarn of claim 77, wherein the one or more electrically non-conductive yarns are no-melt and no-drip according to the ASTM D6413/D6413M Standard Vertical Test Method for Flame Resistance of Textiles.

81. The hybrid yarn of claim 77, wherein the one or more electrically non-conductive yarns have a tensile strength higher than the two or more electrically conductive wires.

82. The hybrid yarn of claim 77, wherein the one or more electrically non-conductive yarns have an elasticity less than that of the wrapped two or more electrically conductive wires such that the two or more electrically conductive wires do not break before the one or more electrically non-conductive yarns under tensile loading of the hybrid yarn.

83. A method of making a machine-knittable hybrid yarn, the method comprising:
    wrapping, in a single process, two or more electrically conductive wires around one or more electrically non-conductive yarns, the electrically conductive wires each having an exterior coated with an insulating material,
    wherein the number of electrically non-conductive yarns is less than the number of electrically conductive wires;
    wherein the electrically non-conductive yarns comprise a majority fraction of an overall cross-section of the hybrid yarn; and
    wherein the one or more electrically non-conductive yarns have an elasticity less than that of the wrapped two or more electrically conductive wires such that the two or more electrically conductive wires do not break before the one or more electrically non-conductive yarns under tensile loading of the hybrid yarn.

84. The method of claim 83, wherein the one or more electrically non-conductive yarns are 1500 denier or finer.

85. The method of claim 83, wherein the one or more electrically non-conductive yarns are fire retardant and self-extinguishing.

86. The method of claim 83, wherein the one or more electrically non-conductive yarns comprise staple fibers.

87. The method of claim 83, wherein the one or more electrically non-conductive yarns are no-melt and no-drip according to the ASTM D6413/D6413M Standard Vertical Test Method for Flame Resistance of Textiles.

88. The method of claim 83, wherein the one or more electrically non-conductive yarns have a tensile strength higher than the two or more electrically conductive wires.

89. A method of making a machine-knittable hybrid yarn, the method comprising:
    wrapping, in a single process, two or more electrically conductive wires around one or more electrically non-conductive yarns, the electrically conductive wires each having an exterior coated with an insulating material,
    wherein the number of electrically non-conductive yarns is less than the number of electrically conductive wires;
    wherein the electrically non-conductive yarns comprise a majority fraction of an overall cross-section of the hybrid yarn; and
    wherein the one or more electrically non-conductive yarns are fire retardant and self-extinguishing.

90. The method of claim 89, wherein the one or more electrically non-conductive yarns are 1500 denier or finer.

91. The method of claim 89, wherein the one or more electrically non-conductive yarns have an elasticity less than that of the wrapped two or more electrically conductive wires such that the two or more electrically conductive wires do not break before the one or more electrically non-conductive yarns under tensile loading of the hybrid yarn.

92. The method of claim 89, wherein the one or more electrically non-conductive yarns have a tensile strength higher than the two or more electrically conductive wires.

93. The method of claim 89, wherein the one or more electrically non-conductive yarns comprise staple fibers.

94. The method of claim 89, wherein the one or more electrically non-conductive yarns are no-melt and no-drip according to the ASTM D6413/D6413M Standard Vertical Test Method for Flame Resistance of Textiles.

95. A method of making a machine-knittable hybrid yarn, the method comprising:
    wrapping, in a single process, two or more electrically conductive wires around one or more electrically non-conductive yarns, the electrically conductive wires each having an exterior coated with an insulating material,
    wherein the number of electrically non-conductive yarns is less than the number of electrically conductive wires;
    wherein the electrically non-conductive yarns comprise a majority fraction of an overall cross-section of the hybrid yarn; and
    wherein the one or more electrically non-conductive yarns have a tensile strength higher than the two or more electrically conductive wires.

96. The method of claim 95, wherein the one or more electrically non-conductive yarns are 1500 denier or finer.

97. The method of claim 95, wherein the one or more electrically non-conductive yarns have an elasticity less than that of the wrapped two or more electrically conductive wires such that the two or more electrically conductive wires do not break before the one or more electrically non-conductive yarns under tensile loading of the hybrid yarn.

98. The method of claim 95, wherein the one or more electrically non-conductive yarns are fire retardant and self-extinguishing.

99. The method of claim 95, wherein the one or more electrically non-conductive yarns comprise staple fibers.

100. The method of claim 95, wherein the one or more electrically non-conductive yarns are no-melt and no-drip according to the ASTM D6413/D6413M Standard Vertical Test Method for Flame Resistance of Textiles.

101. A method of making a machine-knittable hybrid yarn, the method comprising:
    wrapping, in a single process, two or more electrically conductive wires around one or more electrically non-conductive yarns, the electrically conductive wires each having an exterior coated with an insulating material,
    wherein the number of electrically non-conductive yarns is less than the number of electrically conductive wires;
    wherein the electrically non-conductive yarns comprise a majority fraction of an overall cross-section of the hybrid yarn; and
    wherein the one or more electrically non-conductive yarns comprise at least one of: an aramid, meta-aramid, or para-aramid polyamide fiber.

102. The method of claim 101, wherein the one or more electrically non-conductive yarns are 1500 denier or finer.

103. The method of claim 101, wherein the one or more electrically non-conductive yarns have an elasticity less than that of the wrapped two or more electrically conductive wires such that the two or more electrically conductive wires do not break before the one or more electrically non-conductive yarns under tensile loading of the hybrid yarn.

104. The method of claim 101, wherein the one or more electrically non-conductive yarns are fire retardant and self-extinguishing.

105. The method of claim 101, wherein the one or more electrically non-conductive yarns have a tensile strength higher than the two or more electrically conductive wires.

106. The method of claim 101, wherein the one or more electrically non-conductive yarns comprise staple fibers.

107. The method of claim 101, wherein the one or more electrically non-conductive yarns are no-melt and no-drip according to the ASTM D6413/D6413M Standard Vertical Test Method for Flame Resistance of Textiles.

\* \* \* \* \*